(12) United States Patent
Lee (10) Patent No.: US 7,311,735 B2
(45) Date of Patent: Dec. 25, 2007

(54) FEMORAL STEM FOR ARTIFICIAL COXAL ARTICULATION AND METHOD FOR PROCESSING NECK PORTION THEREOF

(75) Inventor: Joong-myung Lee, Seoul (KR)

(73) Assignee: Corentec Co., Ltd. (KR)

( * ) Notice: Subject to any disclaimer, the term of this patent is extended or adjusted under 35 U.S.C. 154(b) by 353 days.

(21) Appl. No.: 11/119,622

(22) Filed: May 2, 2005

(65) Prior Publication Data
US 2005/0267590 A1 Dec. 1, 2005

(30) Foreign Application Priority Data
May 28, 2004 (KR) ............... 10-2004-0038359

(51) Int. Cl.
*A61F 2/36* (2006.01)
(52) U.S. Cl. ................... 623/23.35; 623/23.15
(58) Field of Classification Search ............ 623/23.14, 623/23.05, 23.35; A61F 2/36, 2/32
See application file for complete search history.

(56) References Cited

U.S. PATENT DOCUMENTS 7,060,102 B2 * 6/2006 Thompson et al. ...... 623/23.35

* cited by examiner

*Primary Examiner*—Ehud Gartenberg
*Assistant Examiner*—Jason-Dennis Stewart
(74) *Attorney, Agent, or Firm*—Cantor Colburn LLP (57) ABSTRACT

Disclosed are a femoral stem for artificial coxal articulation, in which portions of the femoral stem interfering with and contacting an insertion in the joint movement of the femoral stem are removed from the femoral stem so as to maximize the range of the joint movement thereof while maintaining the cross sectional area thereof, and a method for processing a neck portion of the femoral stem. The method includes cutting symmetrical portions of the outer circle of a circular rod to form cutting planes inwardly inclined such that the cutting planes contact a virtual inner circle having the same center as that of the outer circle; and rounding a portion between the cutting planes along the inner circle so that the inner part of the outer circle is shorter than the outer part of the outer circle.

8 Claims, 10 Drawing Sheets

FEMORAL STEM FOR ARTIFICIAL COXAL ARTICULATION AND METHOD FOR PROCESSING NECK PORTION THEREOF

BACKGROUND OF THE INVENTION

1. Field of the Invention

The present invention relates to a femoral stem for artificial coxal articulation, and more particularly a femoral stem for artificial coxal articulation, in which portions of the femoral stem interfering with and contacting an insertion in the joint movement of the femoral stem are removed from the femoral stem so as to maximize the range of joint movement thereof while maintaining the cross sectional area thereof, and a method for processing a neck portion of the femoral stem.

2. Description of the Related Art

Figure 1:
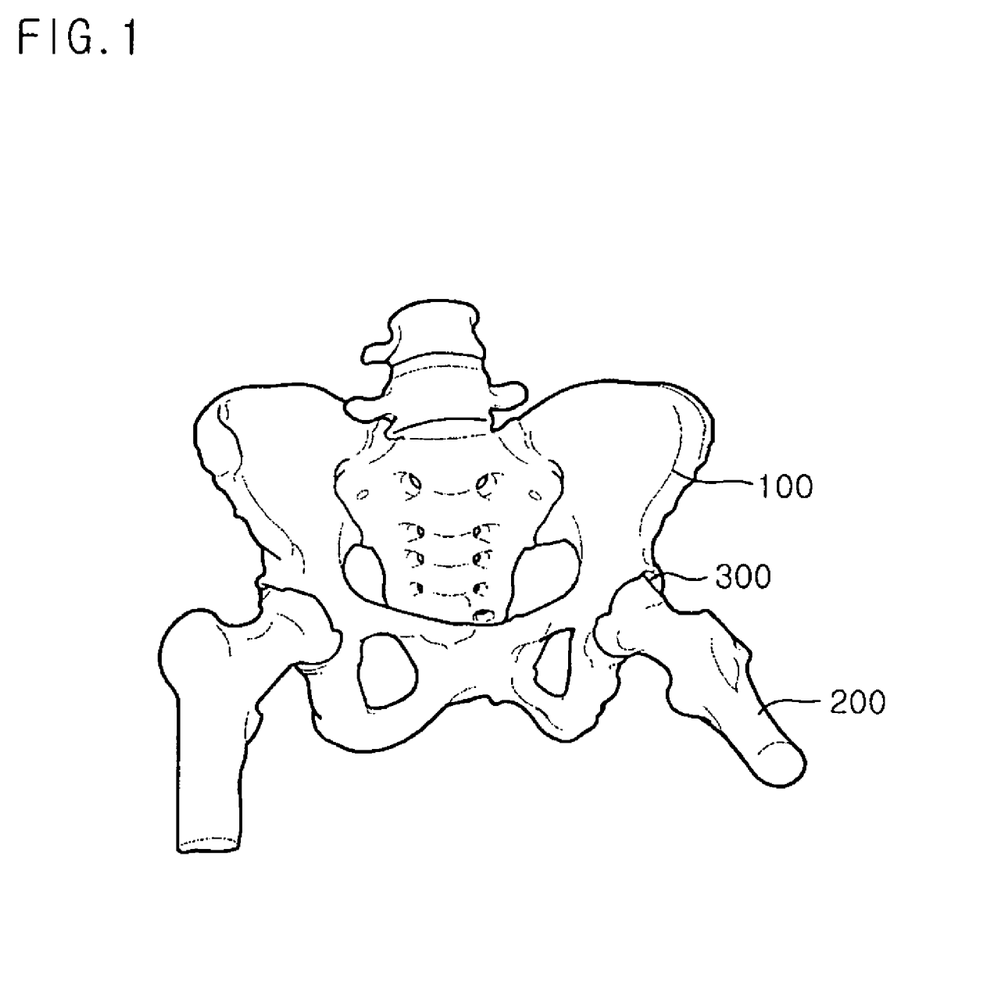
FIG. 1 is a perspective view of a coxal articulation of the human body.

Generally, as shown in FIG. 1, coxal articulation refers to articulation for connecting the femur 200 and the pelvis 100 of a human body, and plays the primary role in sitting or standing. The coxal articulation is damaged by various diseases or external injuries. In order to cure the damaged coxal articulation 300, an artificial coxal articulation is applied through a surgical operation.

Figure 2:
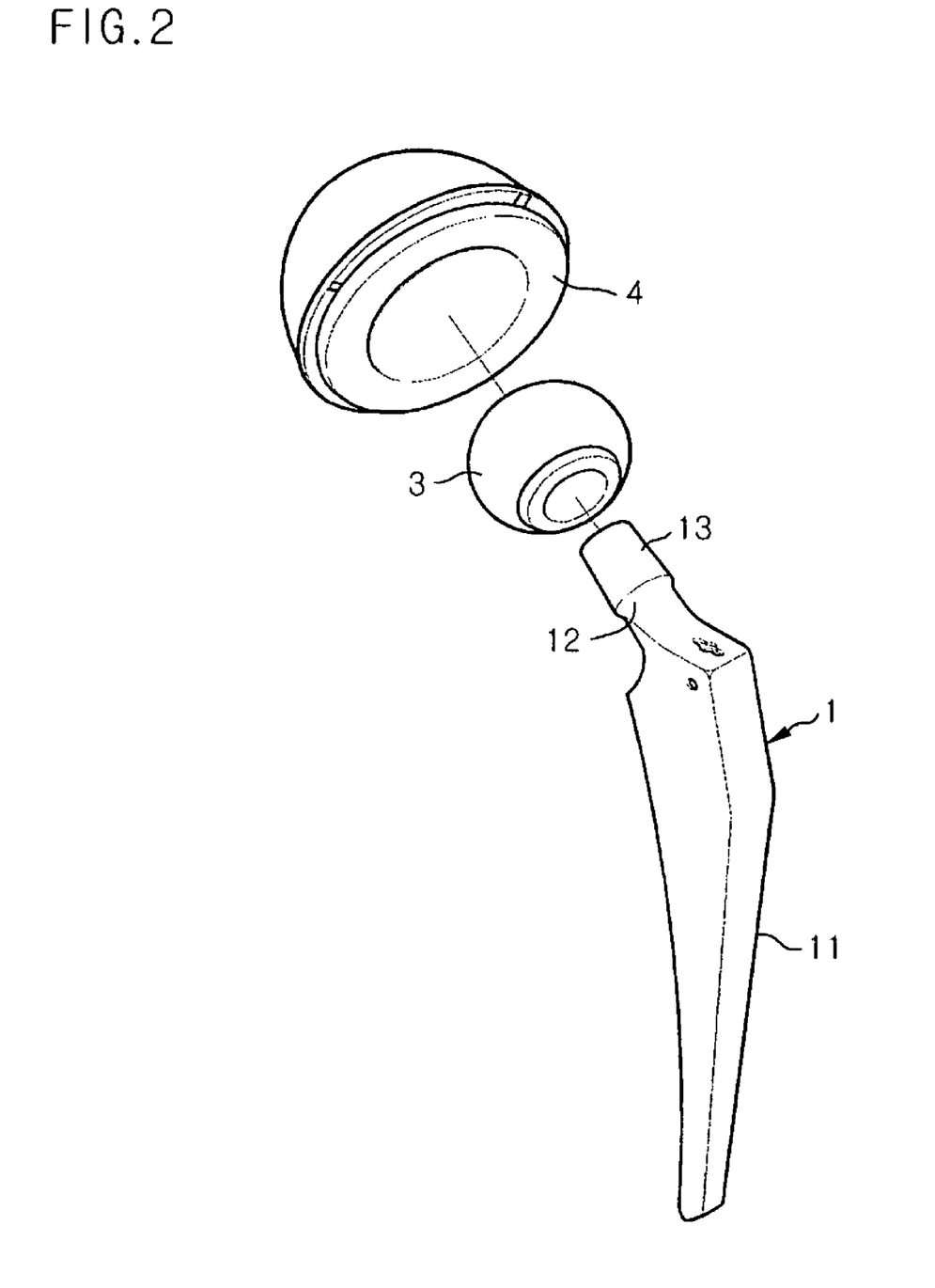
FIG. 2 is an exploded perspective view of a general artificial coxal articulation.

As shown in FIG. 2, the artificial coxal articulation comprises an acetabulum cup 4 fixed to the acetabulum 300 of the pelvis 100, an artificial bone head 3 fixedly inserted into the femur 200, and a femoral stem 1.

An insertion 2 having a hemispheric shape made of ceramic or high molecular weight polyethylene is fixed into the acetabulum cup 4, and the artificial bone head 3 having a spherical shape made of ceramic or metal is formed on one end of the femoral stem 1. The artificial bone head 3 is connected to the insertion 2 such that the artificial bone head 3 is rotated against the insertion 2 according to the movements of the femur 200 and the femoral stem 1.

The most important point of the above-described artificial coxal articulation is how to perform the rotational movement of the artificial coxal articulation in a range similar to the joint movement of coxal articulation of the human body.

Figure 3A:
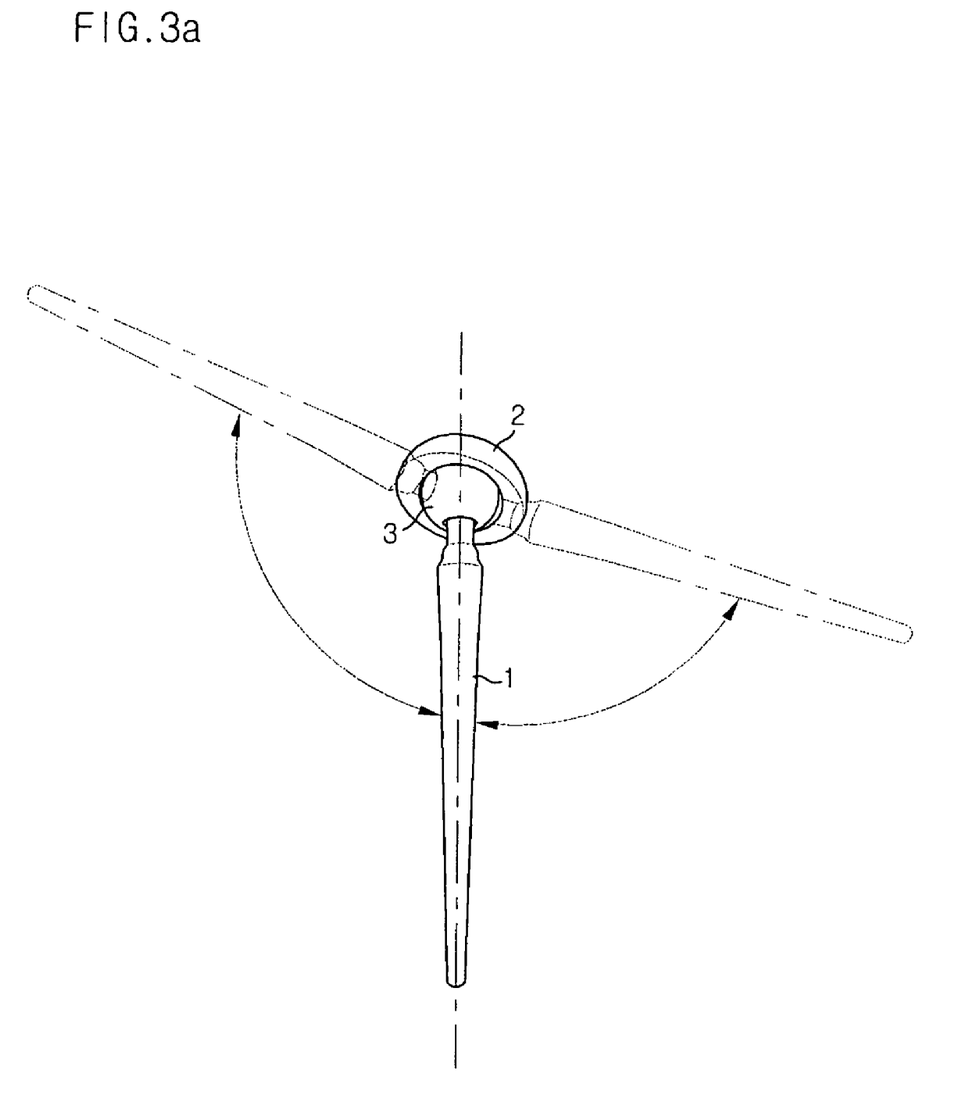
FIGS. 3a to 3c are perspective views illustrating the movement of the artificial coxal articulation.
Figure 3B:
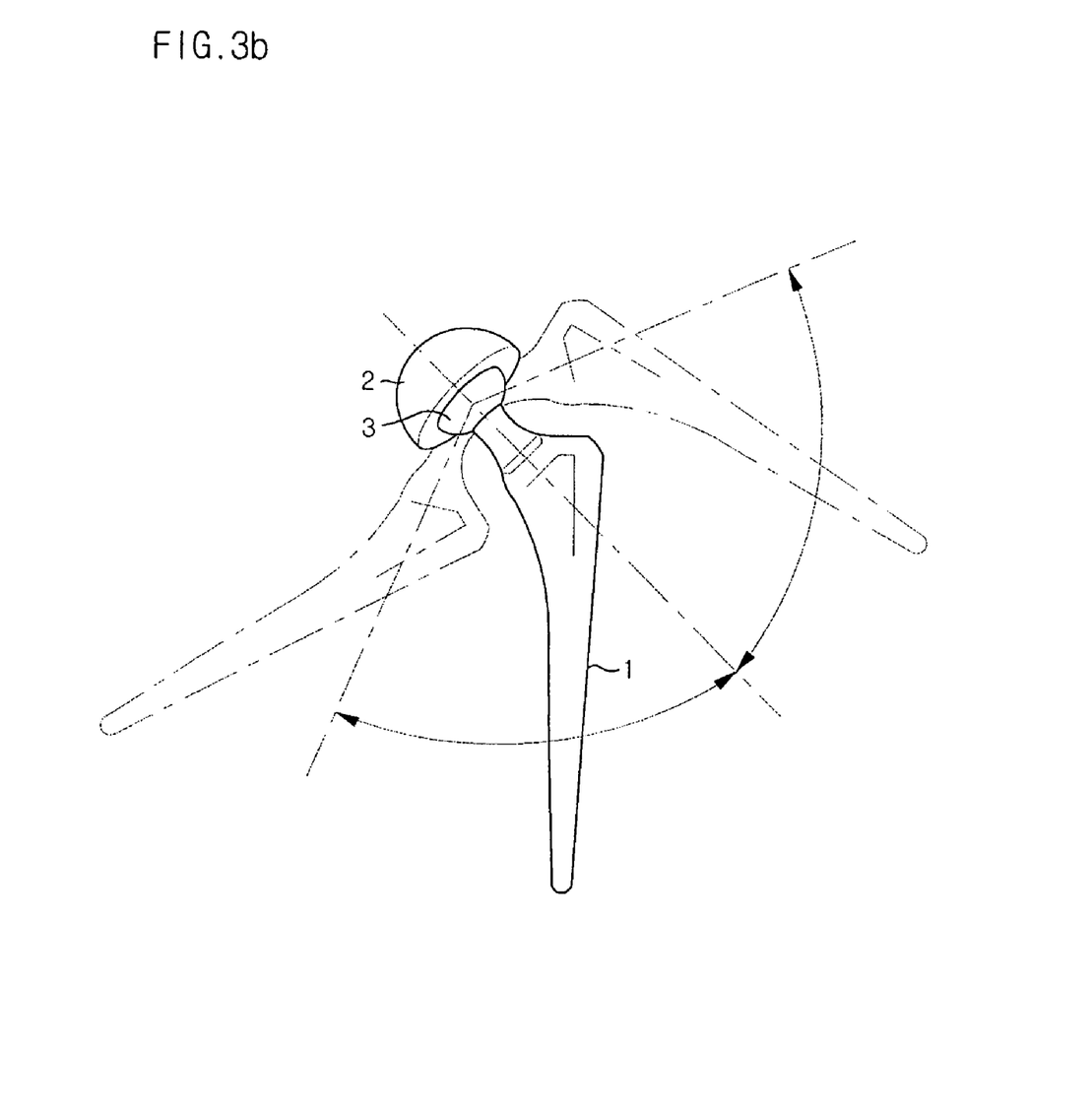
Figure 3C:
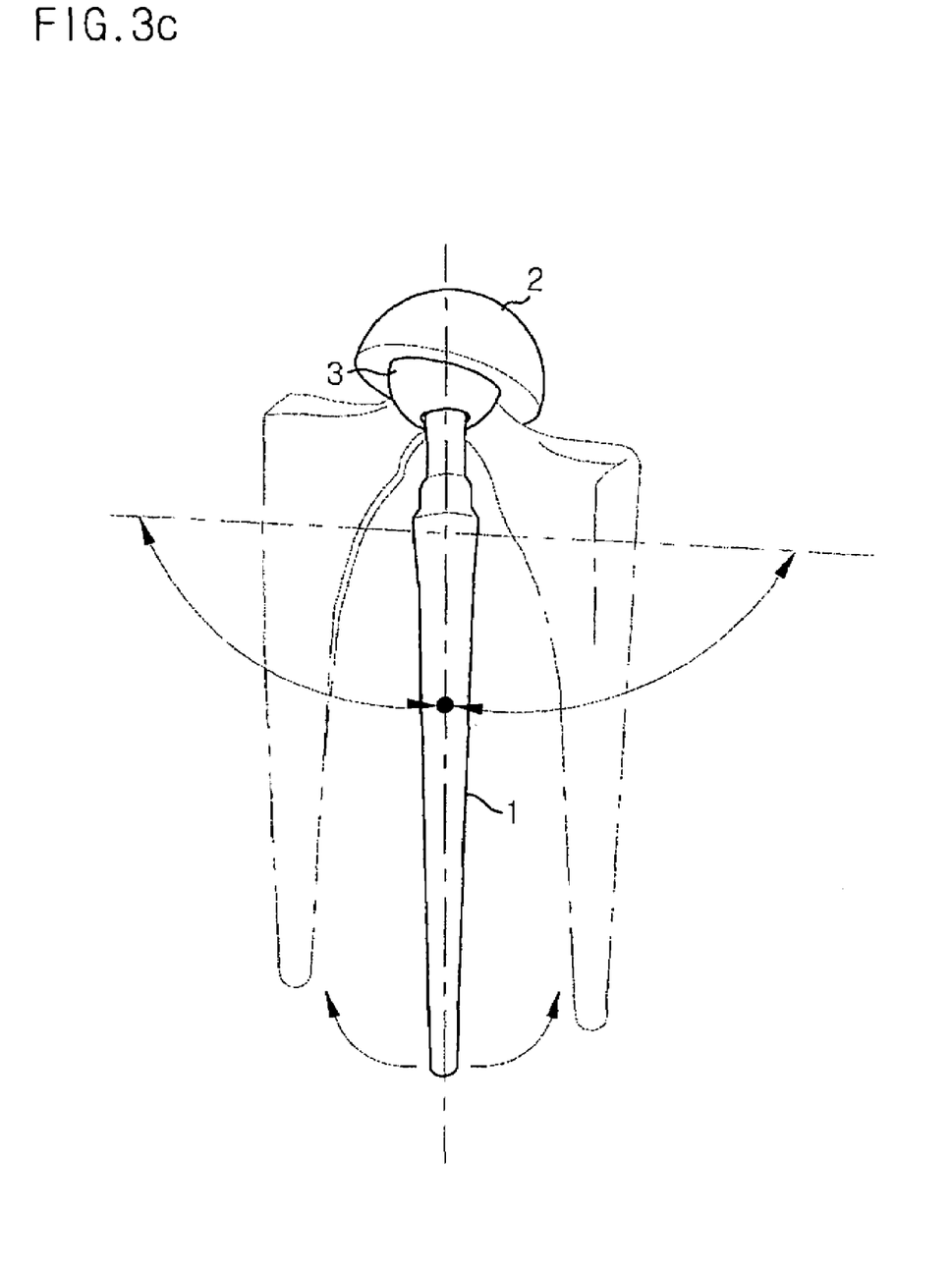

The joint movement of the coxal articulation is divided into flexion in which the femur moves in the front direction of the pelvis and extension in which the femur moves in the reverse direction, as shown in FIG. 3a, adduction in which the femur moves inside the pelvis and abduction in which the femur moves outside the pelvis, as shown in FIG. 3b, and internal rotation in which the femur rotates in the inner direction of the pelvis and external rotation in which the femur rotates in the reverse direction, as shown in FIG. 3c.

Figure 4:
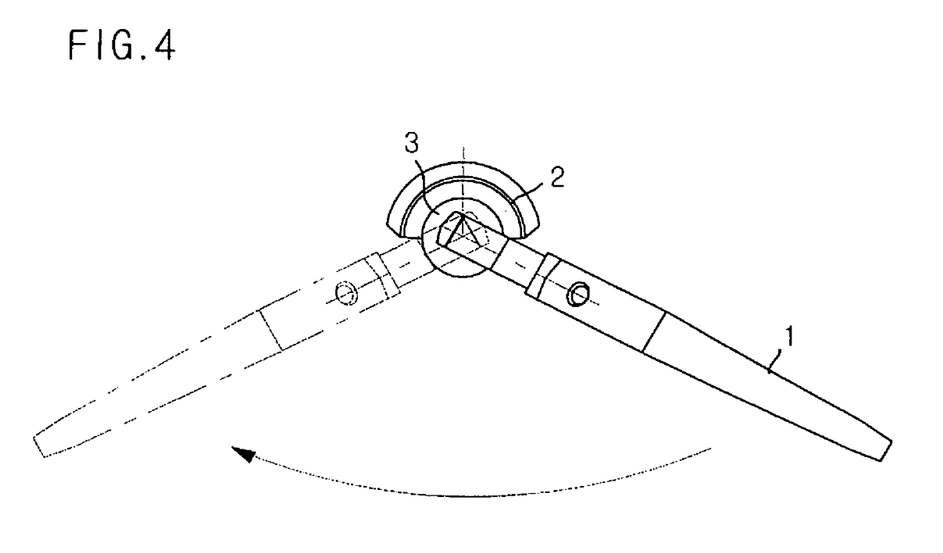
FIG. 4 is a side view illustrating the artificial coxal articulation of FIG. 3a in flexion and extension states.

That is, as shown in FIG. 4, the flexion and extension respectively refer to the movements of the femoral stem 1 in the front and rear directions of the insertion 2, the adduction and abduction respectively refer to the movements of the femoral stem 1 to the inside and outside of the insertion 2, and the internal and external rotations respectively refer to the rotations of the femoral stem 1 in the inner and outer directions of the insertion 2.

Accordingly, the range of rotation of the artificial coxal articulation is determined by a range of the rotational movement of the femoral stem 1, i.e., an angle of rotation of the femoral stem 1. When the femoral stem 1 is manufactured, in order to minimize interference of the femoral stem 1 with the insertion 2, the diameter of a neck portion of the femoral stem 1 is decreased.

As shown in FIG. 2, the femoral stem 1 comprises a femoral stem main body 11 directly and fixedly inserted into the femur, a cutting conical portion 13 formed on one end of the femoral stem main body 11 so that the artificial bone head 3 is inserted into the cutting conical portion 13, and a neck portion 12 formed between the cutting conical portion 13 and the femoral stem main body 11.

Here, the neck portion 12 of the femoral stem 1 contacts the insertion 2 by the joint movement of the femoral stem 1. Accordingly, the smaller the diameter of the neck portion 12, the larger the range of movement of the femoral stem 1. However, when the diameter of the neck portion 12 is excessively small, the neck portion 12 is broken. Accordingly, the diameter of the neck portion 12 has a limit.

Figure 5:
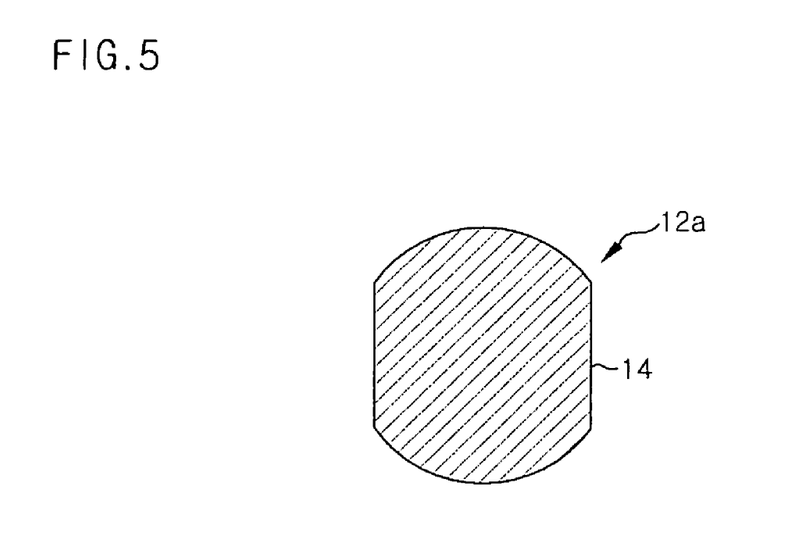
FIG. 5 is a sectional view illustrating one example of the structure of a neck portion of a conventional femoral stem for artificial coxal articulation.

Recently, in order to overcome the above limit, a method, in which the joint movement of the femoral stem 1, particularly the range of the flexion of the femoral stem 1, is increased while the limit of the diameter of the neck portion 12 is maintained, has been proposed. For this reason, as shown in FIG. 5, one example of a sectional structure of a neck portion of the conventional femoral stem 1 is proposed.

As described above, the femoral stem 1 for artificial coxal articulation comprises the femoral stem main body 11, the cutting conical portion 13, and a neck portion 12a having a circular cross section. As shown in FIG. 5, the neck portion 12a has a limit diameter, and includes cutting planes 14 symmetrically formed at both sides thereof directly contacting the insertion 2 when the femoral stem 1 performs joint movement.

Figure 6:
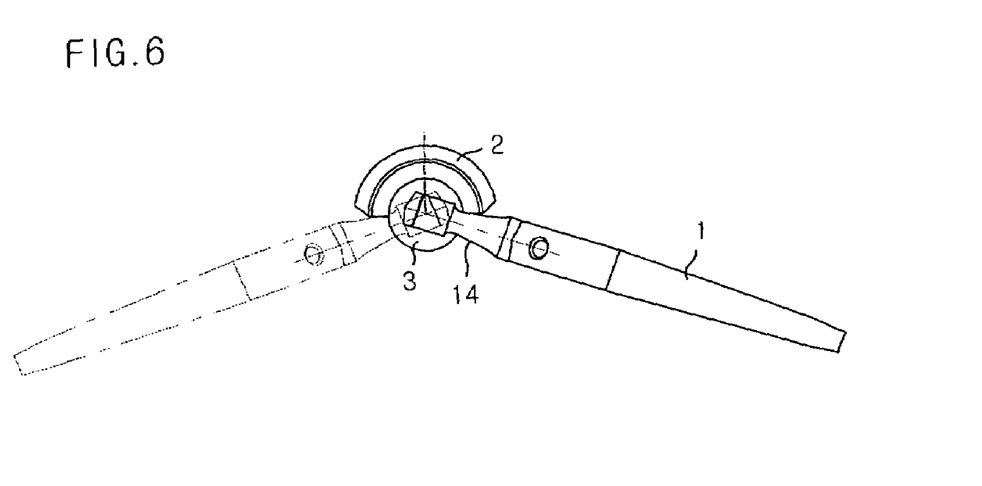
FIG. 6 is a side view illustrating the femoral stem of FIG. 5 in flexion and extension states.

That is, portions of the neck portion 12a contacting the insertion 2 are cut under the condition that the limit diameter of the neck portion 12a is maintained, thereby producing the cutting planes 14. The range of the movement of the femoral stem 1 is expanded in compensation for the cutting of the portions of the neck portion 12a. That is, as shown in FIG. 6, in the flexion of the femoral stem 1, the range of the movement of the femoral stem 1 is increased by approximately 10°.

Figure 7:
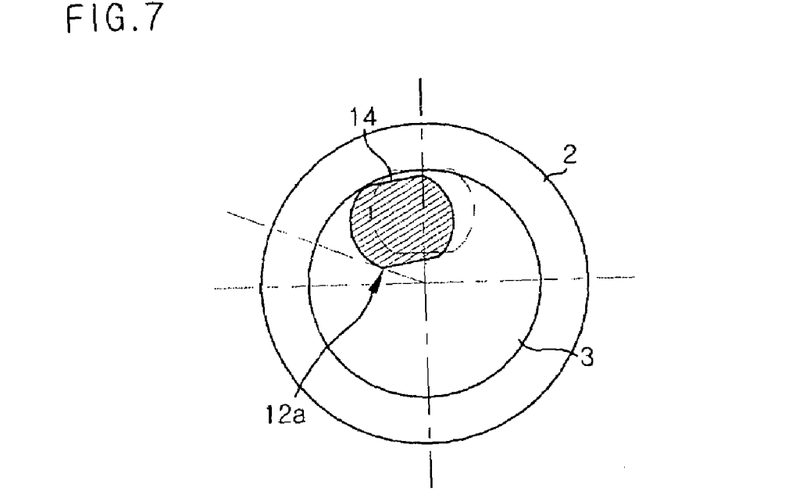
FIG. 7 is a sectional view illustrating the femoral stem in the flexion state, which interferes with an insertion.

However, since the acetabulum cup is inserted into the pelvis at an angle of 40~50° when the artificial coxal articulation is inserted into the pelvis, the acetabulum cap of the femoral stem 1 in the joint movement does not interfere with the front and rear cutting planes 14 of the neck portion 12a, but interferes with corners of the neck portion 12a inwardly turned at an angle of 40~50°, as shown in FIG. 7. Accordingly, the increase in the range of movement of the artificial coxal articulation is substantially no more than approximately 50.

Compared to the coxal articulation of the human body, which has the angle of flexion of approximately 130~135°, the above artificial coxal articulation substantially has the angle of flexion of at most 110°. Accordingly, the above discordance generates interference when the flexion of the artificial coxal articulation is performed.

Such interference generates abrasion of an insertion made of polyethylene in the acetabulum cup, breakage of an insertion made of ceramic in the acetabulum cup, dislocation of artificial coxal articulation, or detachment of the artificial coxal articulation. Accordingly, the increase in the range of movement of the artificial coxal articulation is essential, and, particularly, is important in the East requiring eating life while sitting.

SUMMARY OF THE INVENTION

Therefore, the present invention has been made in view of the above problems, and it is an object of the present invention to provide a femoral stem for artificial coxal articulation, in which portions of the femoral stem interfering with and contacting an insertion in the joint movement of the femoral stem are removed from the femoral stem so as to maximize the range of joint movement thereof while maintaining the cross sectional area thereof, and a method for processing a neck portion of the femoral stem.

In accordance with one aspect of the present invention, the above and other objects can be accomplished by the provision of a method for processing a neck portion of a femoral stem for artificial coxal articulation comprising: cutting symmetrical portions of the outer circle of a circular rod to form cutting planes inwardly inclined such that the cutting planes contact a virtual inner circle having the same center as that of the outer circle; and rounding a portion between the cutting planes along the inner circle so that the inner part of the outer circle is shorter than the outer part of the outer circle.

Preferably, the angle of inclination of the cutting planes may be in the range of 40~50°.

Further, preferably, the outer circle may have a diameter of 13~14 mm, the inner circle may have a diameter of 9~10 mm, and the cutting planes may be obtained by cutting the outer circle to a depth of 1~2 mm.

In accordance with another aspect of the present invention, there is provided a femoral stem for artificial coxal articulation comprising a neck portion processed by the above method.

In accordance with yet another aspect of the present invention, there is provided a femoral stem for artificial coxal articulation comprising: a femoral stem main body; a cutting conical portion; and a neck portion, wherein the neck portion has a cross sectional structure such that cutting planes inwardly inclined and symmetrical to each other are formed in front and rear portion of a circular rod, and a rounding portion is formed between the cutting planes along an inner circle having the same center as that of the circular rod and a diameter smaller than that of the circular rod.

Preferably, the angle of inclination of the cutting planes may be in the range of 40~50°.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Now, a method for processing a neck portion of a femoral stem for artificial coxal articulation of the present invention will be described in detail with reference to the annexed drawings.

Figure 8:
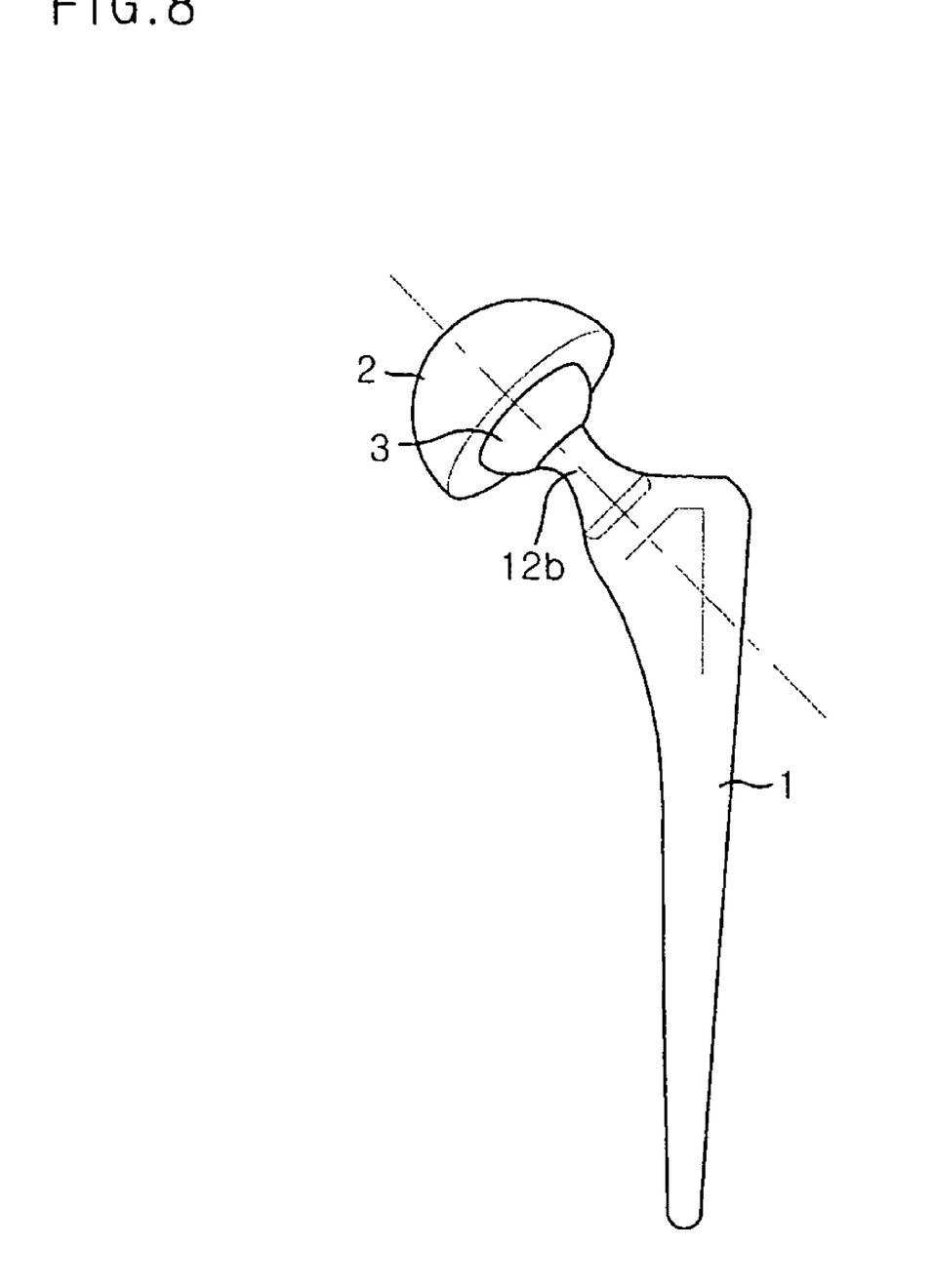
FIG. 8 is a front view of a femoral stem for artificial coxal articulation in accordance with the present invention.

FIG. 8 is a front view of a femoral stem for artificial coxal articulation processed in accordance with the present invention. Similarly to the conventional femoral stem, the femoral stem of the present invention a femoral stem main body 11 directly and fixedly inserted into the femur, a cutting conical portion (not shown) formed on one end of the femoral stem main body 11 so that an artificial bone head 3 is inserted into the cutting conical portion, and a neck portion 12b formed between the cutting conical portion and the femoral stem main body 11. Here, the artificial bone head 3 slidably contacts an insertion 2, and is rotated.

Portions of the above-described femoral stem, which interfere with and contact the insertion 2 in the joint movement of the femoral stem, are removed from the femoral stem so as to maximize the range of joint movement thereof while maintaining the cross sectional area of the femoral stem. Hereinafter, the femoral stem will be described in more detail.

Figure 9:
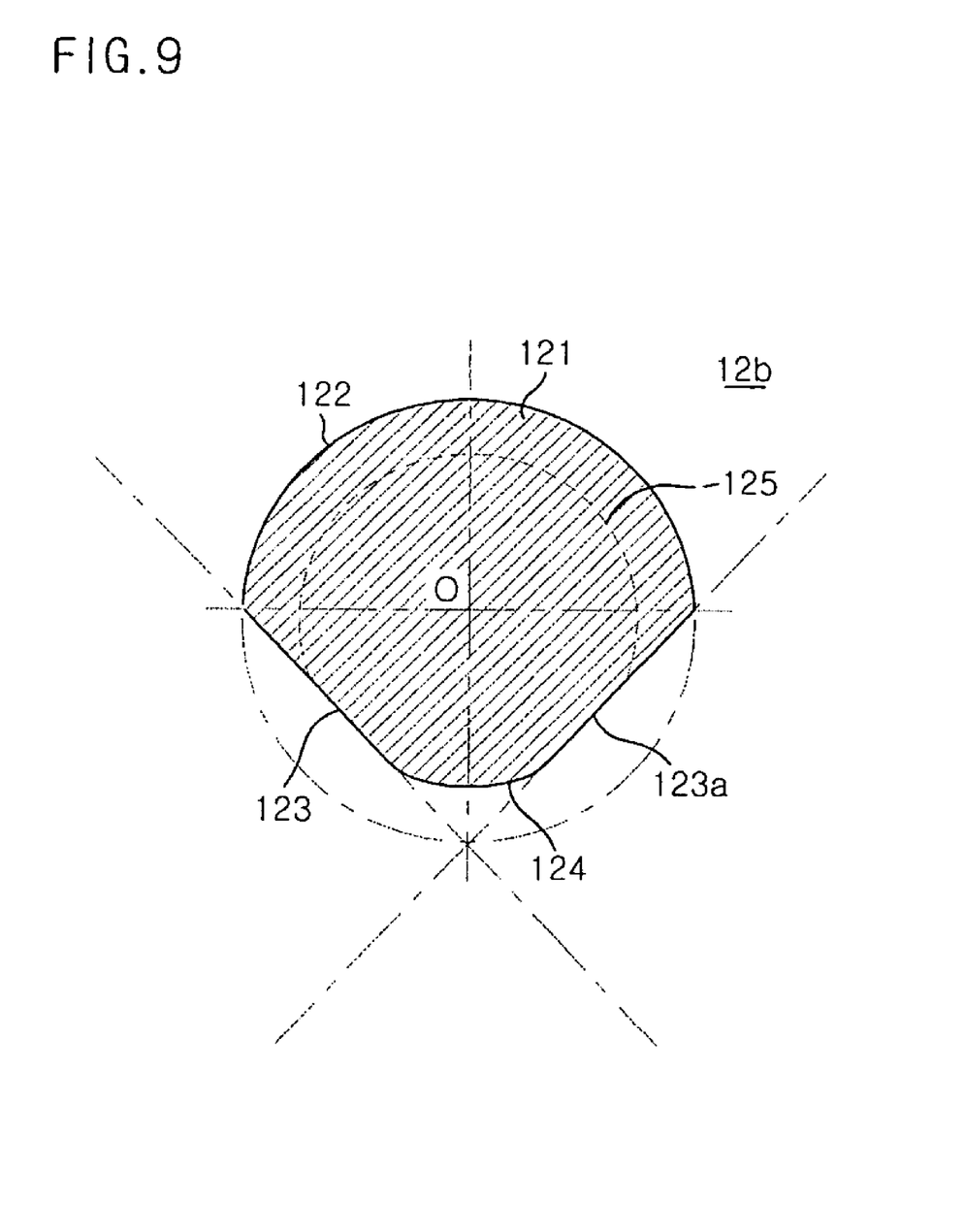
FIG. 9 is a sectional view of a neck portion of the femoral stem in accordance with the present invention.
Figure 10:
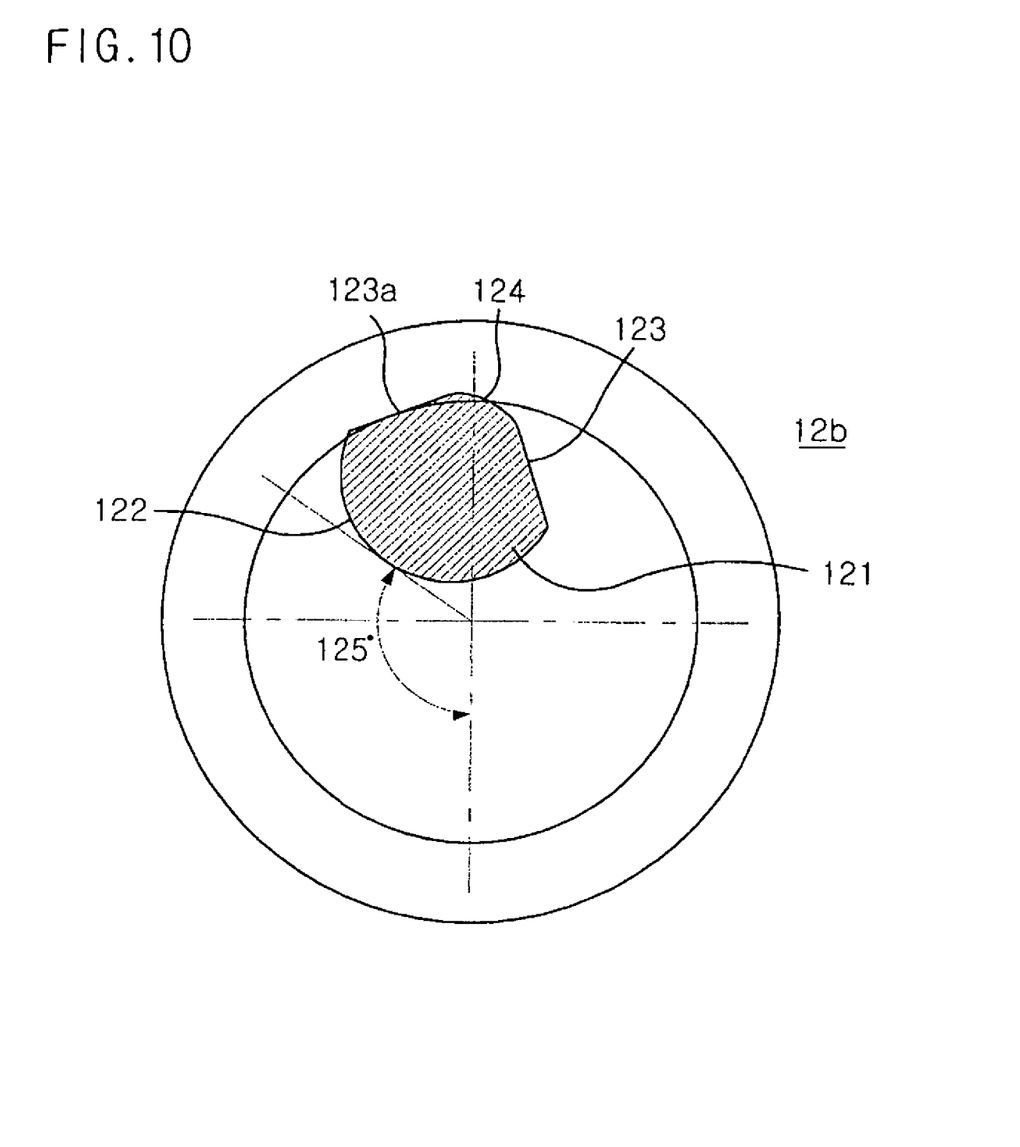
FIG. 10 is a sectional view of the femoral stem in a flexion state in accordance with the present invention.

FIG. 9 is a sectional view of the neck portion of the femoral stem in accordance with the present invention.

As shown in FIG. 9, the neck portion 12b of the femoral stem of the present invention has a sectional structure such that cutting planes 123 and 123a are symmetrically formed on front and rear portions of a circular rod 121 and are inclined inwardly, and a rounding portion 124 is formed between the cutting planes 123 and 123a. A method for processing the neck portion 12b having the above sectional structure will be described as follows.

First, the cutting planes 123 and 123a are formed by cutting portions of the circular rod 121 contacting an outer circle 122 having the same diameter as that of the circular rod 121. Here, the obtained cutting planes 123 and 123a contact an inner circle 125 having the same center as that of the outer circle 122, and the cutting depth of the portions of the circular rod 121 varies according to the movement of the cutting planes 123 and 123a due to the variation in the inner circle 125.

The angle of inclination of the cutting planes 123 and 123a is in the range of 40~50°. The above angle of inclination is an offset angle of the portions of the neck portion 12b interfering with and contacting the insertion 2, which has an angle of inclination of 45° when the artificial coxal articulation is inserted into the pelvis, in the joint movement of the artificial coxal articulation. The above range of 40~50° of the angle of inclination of the cutting planes 123 and 123a allows the strength of the neck portion 12b to be changed when the femoral stem is designed.

The rounding portion 124 is formed by cutting the circular rod 121 along the radius of the inner circle 125 between the cutting planes 123 and 123a located inside the outer circle 122. Thereby, as shown in FIG. 9, the inner radius of the outer circle 122 is shorter than the outer radius of the outer circle 122 so that inner and outer portions of the outer circle 122 are asymmetrical.

Preferably, the outer circle 122 has a diameter of 13~14 mm, the inner circle 125 has a diameter of 9~10 mm, and the cutting planes 123 and 123a are obtained by cutting the portions of the circular rod 121 to a depth of 1~2 mm.

The cross sectional area of the neck portion of the conventional femoral stem, having an approximately circular shape with a diameter of 11 mm, was 95 mm². On the other hand, the cross sectional area of the neck portion 12b of the femoral stem of the present invention was approximately 99 mm², which is larger than that of the conventional neck portion. Further, in the flexion of the femoral stem, the angle of rotation of the neck portion of the conventional femoral stem was 112°. On the other hand, in the flexion of the femoral stem, the angle of rotation of the neck portion 12b was 125°, which is larger than that of the conventional neck portion by 13°.

The limit diameter of the neck portion of the conventional femoral stem was approximately 11 mm. However, the neck portion 12b of the femoral stem of the present invention had a limit diameter of 9 mm. The neck portion 12b having a diameter of 9 mm has a cross sectional area larger than that of the neck portion of the conventional femoral stem having a diameter of 11 mm, and has an angle of rotation in flexion larger than that of the neck portion of the conventional femoral stem by 13°. Hereinafter, the above results will be stated in more detail with reference to Table 1.

TABLE 1

| Diameter (mm) | Cross sectional area (mm²) |
|---|---|
| Φ9 | 63.6 |
| Φ10 | 78.5 |
| Φ11 | 95.0 |
| Φ12 | 113.1 |
| Φ13 | 132.7 |

According to the above Table 1, the cross sectional portion of a conventional neck portion having an approximately circular shape with a diameter of 13 mm was 132.7 mm², the cross sectional portion of a conventional neck portion having an approximately circular shape with a diameter of 11 mm was 95.0 mm², the cross sectional portion of a conventional neck portion having an approximately circular shape with a diameter of 10 mm was 78.5 mm², and the cross sectional portion of a conventional neck portion having an approximately circular shape with a diameter of 9 mm was 63.6 mm². Here, the conventional neck portion with a diameter of 9 mm has low strength, thus not being substantially applied.

The neck portion of the femoral stem of the present invention has a diameter of 9 mm, which is smaller than the limit diameter (10 mm) of the neck portion of the conventional femoral stem, but has a cross sectional area of approximately 99 mm², which is larger than that (95.0 mm²) of the neck portion having a diameter of 11 mm of the convention femoral stem. Accordingly, the neck portion of the femoral stem of the present invention maintains the cross sectional area thereof, and maximizes the range of the movement thereof, which will be described later.

TABLE 2

| | Femoral stem of the present invention having artificial bone head having diameter of 32 mm | Conventional femoral stem having artificial bone head having diameter of 32 mm | Femoral stem of the present invention having artificial bone head having diameter of 28 mm | Conventional femoral stem having artificial bone head having diameter of 28 mm |
|---|---|---|---|---|
| Normal flexion | 130° | 118° | 125° | 112° |
| Normal extension | 89° | 77° | 83° | 70° |
| 6 & 10 flexion | 129° | 118° | 125° | 112° |
| 6 & 10 extension | 71° | 63° | 65° | 57° |
| Normal adduction | 71° | 64° | 69° | 60° |
| Normal abduction | 64° | 64° | 60° | 60° |
| 6 & 10 adduction | 63° | 56° | 61° | 52° |
| 6 & 10 abduction | 69° | 69° | 65° | 65° |
| Normal internal rotation | 119° | 118° | 112° | 112° |
| Normal external rotation | 77° | 77° | 70° | 70° |
| 6 & 10 internal rotation | 135° | 134° | 127° | 126° |
| 6 & 10 external rotation | 76° | 76° | 68° | 68° |

The above Table 2 compares the angle of rotation between the femoral stems of the present invention and the conventional femoral stems. Here, the angle of rotation refers to an angle, at which an acetabulum cup is substantially inserted into the pelvis when the artificial coxal articulation is applied to the human body.

That is, results of the above Table 2 were obtained by inserting an acetabulum cup having a diameter of 56 mm into the acetabulum of the pelvis by downwardly inclining the acetabulum cup at an angle of 45° and then forwardly inclining the acetabulum cup at an angle of 15°, and by inserting a femoral stem into the femur by inwardly inclining the femoral stem at an angle of 6° and then forwardly turning the femoral stem at an angle of 10°.

According to Table 2, the angle of rotation of a conventional femoral stem having an artificial bone head having a diameter of 28 mm in the flexion of the femoral stem was 112°. On the other hand, the angle of rotation of a femoral stem of the present invention having an artificial bone head having a diameter of 28 mm in the flexion of the femoral stem was 125°, which is larger than that of the conventional femoral stem by 13°. Further, the angle of rotation of a conventional femoral stem having an artificial bone head having a diameter of 32 mm in the flexion of the femoral stem was 118°. On the other hand, the angle of rotation of a femoral stem of the present invention having an artificial bone head having a diameter of 32 mm in the flexion of the femoral stem was 129°, which is larger than that of the conventional femoral stem by 11°. Accordingly, the angles of rotation of the femoral stems of the present invention are approximately similar to the angle of rotation (130~135°) of coxal articulation of the human body.

As apparent from the above description, the present invention provides a femoral stem for artificial coxal articulation, in which portions of the femoral stem interfering with and contacting an insertion in the joint movement of the femoral stem are removed from the femoral stem so as to maximize the range of the joint movement thereof while maintaining the cross sectional area thereof, and a method for processing a neck portion of the femoral stem, thereby reducing several problems generated due to the interference caused by the small range of movement of conventional artificial coxal articulation, for example, abrasion of an insertion made of polyethylene in the acetabulum cup, breakage of an insertion made of ceramic in the acetabulum cup, dislocation of the artificial coxal articulation, and detachment of the artificial coxal articulation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for processing a neck portion of a femoral stem for artificial coxal articulation comprising:
    cutting symmetrical portions of the outer circle of a circular rod to form cutting planes inwardly inclined such that the cutting planes contact a virtual inner circle having the same center as that of the outer circle; and
    rounding a portion between the cutting planes along the inner circle so that the inner part of the outer circle is shorter than the outer part of the outer circle.

2. The method as set forth in claim 1, wherein the angle of inclination of the cutting planes is in the range of 40~50°.

3. The method as set forth in claim 1, wherein the outer circle has a diameter of 13~14 mm, the inner circle has a diameter of 9~10 mm, and the cutting planes are obtained by cutting the outer circle to a depth of 1~2 mm.

4. A femoral stem for artificial coxal articulation comprising a neck portion processed by the method as set forth in claim 1.

5. A femoral stem for artificial coxal articulation comprising:
    a femoral stem main body;
    a cutting conical portion; and
    a neck portion,
    wherein the neck portion has a cross sectional structure such that cutting planes inwardly inclined and symmetrical to each other are formed in front and rear portion of a circular rod, and a rounding portion is formed between the cutting planes along an inner circle having the same center as that of the circular rod and a diameter smaller than that of the circular rod.

6. The femoral stem as set forth in claim 5, wherein the angle of inclination of the cutting planes is in the range of 40~50°.

7. A femoral stem for artificial coxal articulation comprising a neck portion processed by the method as set forth in claim 2.

8. A femoral stem for artificial coxal articulation comprising a neck portion processed by the method as set forth in claim 3.

* * * * *